United States Patent
Cheng et al.

(10) Patent No.: US 8,342,007 B2
(45) Date of Patent: Jan. 1, 2013

(54) ELECTROCHEMICAL DETECTION CELL FOR LIQUID CHROMATOGRAPHY SYSTEM

(75) Inventors: Jun Cheng, San Jose, CA (US); Petr Jandik, Los Gatos, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 416 days.

(21) Appl. No.: 12/703,668

(22) Filed: Feb. 10, 2010

(65) Prior Publication Data

US 2011/0192722 A1    Aug. 11, 2011

(51) Int. Cl.
*G01N 30/00* (2006.01)
(52) U.S. Cl. ......... 73/61.52; 422/68.1; 422/70; 210/656
(58) Field of Classification Search .............. 73/61.52; 422/68.1, 70; 210/656; 96/101
See application file for complete search history.

(56) References Cited

U.S. PATENT DOCUMENTS

| | | | |
|---|---|---|---|
| 4,404,065 A | 9/1983 | Matson | |
| 4,497,199 A * | 2/1985 | Matson | 73/61.55 |
| 5,368,706 A | 11/1994 | Bowers et al. | |
| 6,387,625 B1 | 5/2002 | Eckhardt et al. | |
| 6,572,748 B1 | 6/2003 | Herrmann et al. | |
| 7,638,750 B2 | 12/2009 | Kline | |
| 2005/0012543 A1 | 1/2005 | Stearns et al. | |
| 2007/0012349 A1 | 1/2007 | Gaudiana et al. | |
| 2007/0102293 A1* | 5/2007 | Tai et al. | 204/409 |
| 2008/0182136 A1* | 7/2008 | Arnold et al. | 429/7 |
| 2008/0264148 A1 | 10/2008 | Bulst et al. | |
| 2008/0283413 A1 | 11/2008 | Suzuki et al. | |
| 2009/0020438 A1 | 1/2009 | Hodges | |
| 2010/0206355 A1 | 8/2010 | Johnson | |

OTHER PUBLICATIONS

"ED50A Electrochemical Detector Operator's Manual," rev. 02, Nov. 2002, pp. 2-15 to 2-18, 5-7 to 5-18, B17 to B28, Dionex Corporation (available at http://www.dionex.com/en-us/webdocs/57752-31772_02_ED50A_V17.pdf).

"$Pd/H_2$ Reference Electrode," date unknown, Cormet Testing Systems, Helsinki, Finland (see http://www.cormet.fi/pdf/PDF_Pd-H2.pdf).

Bohs et al., "The UniJet: A New Electrochemical Detector for Microbore Liquid Chromatography," Current Separations, 1994, vol. 12, pp. 181-186.

Bowers, "A new analytical cell for carbohydrate analysis with a maintenance-free reference electrode," J. Pharmaceutical & Biomedical Anal., 1991, vol. 9, Nos. 10-12, pp. 1133-1137.

Dobson et al., "Plateau Potentials of the $\alpha+\beta$ Palladium Hydride Electrode at Temperatures between 25 and 195° C.," J. Chem. Soc., Faraday Trans. 1, 1972, vol. 68, pp. 764-772.

Dobson et al., "Some Experimental Factors which Govern the Potential of the Palladium Hydride Electrode at 25 to 195° C.," J. Chem. Soc., Faraday Trans. 1, 1972, vol. 68, pp. 749-763.

Dobson, "The PallapHode Electrode System," Platinum Metals Rev., 1981), vol. 25, No. 2, pp. 72-73.

(Continued)

*Primary Examiner* — David A. Rogers
*Assistant Examiner* — Rodney T Frank
(74) *Attorney, Agent, or Firm* — Morgan, Lewis & Bockius LLP; Victor E. Johnson

(57) ABSTRACT

A detection cell for a chromatography system includes a cell body having an inlet, an outlet, and a counter electrode, a working electrode, a sample flow passageway extending between the inlet and the outlet and in fluid contact with the counter and working electrodes, and a palladium/noble metal reference electrode system. A method of using the detection cell is also described.

19 Claims, 3 Drawing Sheets

OTHER PUBLICATIONS

Fleischmann et al., "A palladium-hydrogen probe electrode for use as a microreference electrode," J. Scientific Instruments, 1968, series 2, vol. 1, pp. 667-668.

Giner, J., "A Practical Reference Electrode," Electrochem. Soc., 1964, vol. 111, p. 376.

Goffe et al., "Internally charged palladium hydride reference electrode—Part 1: The effect of charging current density on long-term stability," Medical & Biological Engineering & Computing, 1978, vol. 16, pp. 670-676.

Ives et al., Reference Electrodes Theory and Practice, 1961, p. 111, Academic Press, New York.

Kelly et al., "Internally charged palladium hydride reference electrode: II Automatically controlled palladium hydride electrode," Medical & Biological Engineering & Computing, 1981, vol. 19, pp. 333-339.

Lunte et al, "Difference Mode Detection with Thin-Layer Dual-Electrode Liquid Chromatography/Electrochemistry," Anal. Chem., 1985, vol. 57, pp. 1541-1546.

Munasiri et al., "Palladium-hydrogen electrodes for coulometric titration analysis of acids and bases," J. Electroanal. Chem., 1992, vol. 332, pp. 333-337.

Otterson et al., "Absorption of Hydrogen by Palladium up to Hydrogen-Palladium Atom Ratios of 0.97," 1969, p. 1-15, NASA, Washington, DC.

Sawyer et al., "Experimental electrochemistry for chemists," 1974, p. 34, Wiley, New York.

Schwing et al., "Comparison of Different Palladium-Hydrogen Electrode as pH Indicators," Analytica Chimica Acta, 1956, vol. 15, pp. 379-388.

Stock et al., "The Palladium Electrode in Aqueous and Non-Aqueous Titrimetry," Analytica Chimica Acta, 1959, vol. 20, pp. 73-78.

Welch et al., "Comparison of Pulsed Coulometric Detection and Potential-Sweep Pulsed Coulometric Detection for Underivatized Amino Acids in Liquid Chromatography," Anal. Chem., 1989, vol. 61, pp. 555-559.

* cited by examiner

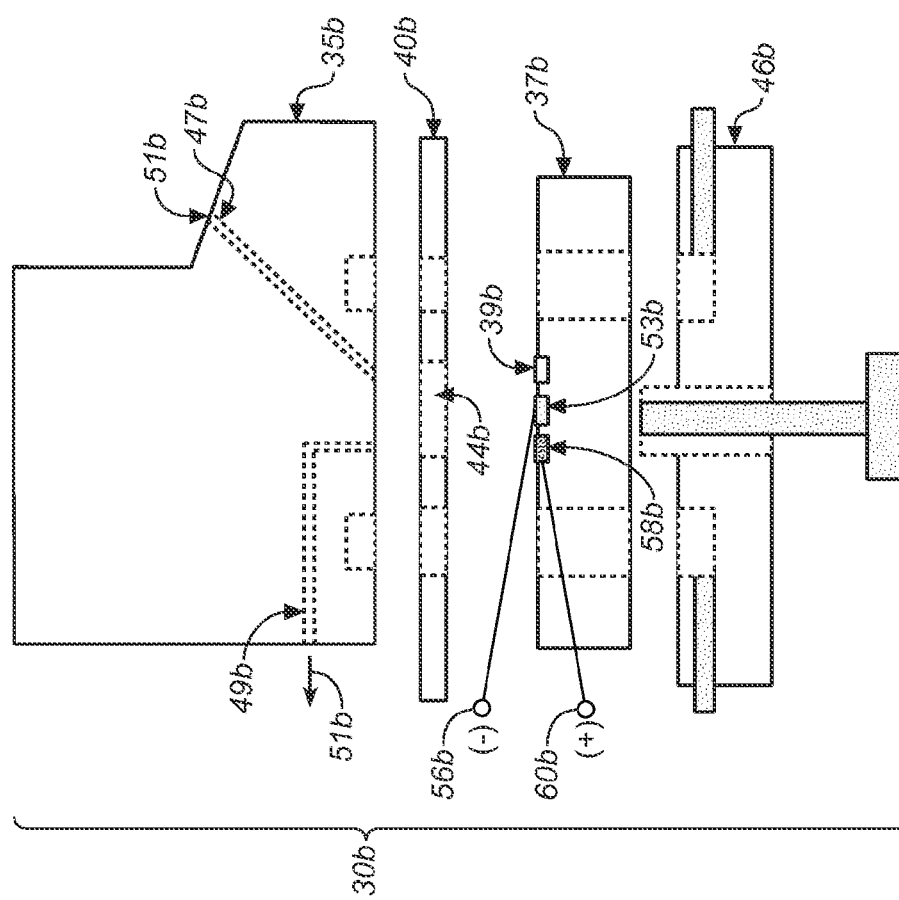

ELECTROCHEMICAL DETECTION CELL FOR LIQUID CHROMATOGRAPHY SYSTEM

BACKGROUND OF THE INVENTION

1. Field of the Invention

This invention relates, in general, to detection cells for liquid chromatography detection and more particularly to reference electrode configurations and methods for their use.

2. Description of Related Art

Liquid chromatographic analysis of carbohydrates, amino acids and related compounds has an important place among the tools utilized in biotechnology industry, biochemical research and in clinical laboratories. Use of liquid chromatographic columns in combination with pulsed electrochemical detection in three-electrode detection cells under alkaline conditions makes possible separations of unique selectivity and direct detection without derivatization of separated analytes with unsurpassed sensitivity. Until now, the prevailing approach to amperometric detection in highly alkaline mobile phases uses a gold working electrode, a platinum or a titanium counter electrode, and a reference electrode of the second kind such as a silver-silver chloride electrode, mercury-mercurous chloride electrode, mercury-mercurous sulfate electrode or thallium amalgam-thallous chloride electrode. Electrodes of the second kind are electrodes in which the chemical element (mostly metal) in the solid phase is in equilibrium with its sparingly soluble salt placed in the liquid phase (see, e.g., SAWYER et al., "Experimental electrochemistry for chemists," 1974, p. 34, Wiley, New York). Over the years, working and counter electrodes have been subject of significant innovations and improvements whereas there were relatively fewer improvements of the reference electrode.

With the increasing importance of capillary chromatography and of hyphenated detection techniques, there is a need to miniaturize the detection cells for carbohydrate, amino acid and related compound analysis. However, miniaturization of cells containing a reference electrode of the second kind is generally very difficult due to the space requirements and surface roughness of liquid junctions and because of general bulkiness of the reference electrode body. There have been attempts to utilize reference electrode of the second kind without a liquid junction. The reference electrode than becomes only a solid phase combination of a metal with a layer of its salt in contact with the test solution (see, e.g., BOHS et al., "The UniJet: A New Electrochemical Detector for Microbore Liquid Chromatography," Current Separations, 1994, vol. 12, pp. 181-186). One of the serious drawbacks of this approach is a requirement of the presence of a counter anion in the test solution. For example for the Ag/AgCl electrode, a sufficient and constant chloride concentration must be maintained in the test solution. The mandated presence of chloride precludes the use of working electrode which could be contaminated by that anion, for example, gold or platinum. Additionally, the sparingly soluble salt involved in one of the equilibriums of electrode of second kind dissolves much more rapidly in a liquid stream than in the static solution forming the liquid junction. Correspondingly, the electrodes of the second kind are much less durable than the same type of electrodes with a liquid junction.

Silver-silver chloride reference electrodes can undergo a change, usually a positive shift, of reference potential during their exposure to alkaline eluents used in chromatographic carbohydrate and amino acid analysis. This leads to excessive potentials being applied to the working electrodes resulting in a gradually decreasing response and/or in narrowing of range of linearity of calibration plots. In extreme cases, working electrodes can be passivated with a loss of detection sensitivity. Other types of reference electrodes such as, for example, mercury-mercurous-chloride electrodes (calomel electrodes), mercury-mercurous sulfate electrodes, and thallium amalgam-thallous chloride electrodes (Thalamid® electrodes) can be affected by alkaline eluents in a similar fashion and affect the functioning of the working electrodes in the same way. All of the above types of reference electrodes include solutions of conductive salts enclosed in liquid junctions forming the interface between the solid parts of the electrode and the electrolyte on the outside. The liquid junctions are known to exude solutions of conductive salts into the electrode surroundings. If such electrode is positioned in a liquid stream inside a detection cell, the salts from the liquid junction can affect functioning of another detector such as mass spectrometer downstream from the detection cell. If the flow through the detector cell is stopped, such as during interruptions of work during a day or overnight, the ionic content of a liquid junction may even contaminate the surface of the working electrode positioned upstream of the reference electrode affecting its behavior during the subsequent period of use. A gold electrode exposed to a contamination by chloride ions exuded from a liquid junction of a reference electrode can serve as an example. Lastly, the constant diffusion of the ions from the liquid junction predetermines the limited lifetime of a reference electrode of the second kind. Its reference potential can remain in the useful range only as long as the concentration of the conductive salt in the liquid junction remains above a certain minimum value.

Another problem with silver-silver chloride reference electrodes and all other reference electrodes of the second kind is the difficulty to design miniaturized detection cells with minimal dead volume using such electrodes. Minimal dead volume is important for preventing peak broadening and other types of peak shape deformation measured as a loss of chromatographic efficiency. Poor chromatographic efficiency leads among other things to poor separation between peaks and to a corresponding decrease in quantitative precision and accuracy of results based on the measurement of peak areas of separated compounds of interest. Available designs of liquid junctions (roughness, bulkiness) generally make it impossible to minimize dead volume to fulfill the requirements of capillary format of high-performance liquid chromatography.

Yet another disadvantage of conventional reference electrodes of the second kind is that the presence of relatively high concentration of potentially electrode contaminating ions exuding from the reference electrode body is decreasing the number of available options for the relative positioning of electrodes of a three electrode cell. A reference electrode of the second kind always has to be positioned downstream from the working electrode(s). The reference electrodes of the second kind also make serial connections of two or more electrochemical detection cells more difficult for the same reason.

In contrast to reference electrodes of the second kind, reference electrodes of the first kind do not exhibit the same bulkiness of the electrode body and do not require liquid junctions. The reference electrodes of the first kind have a metallic or soluble phase of the electrode in a direct equilibrium with its ion (for example $H_2$ and $H^+$; see, e.g., SAWYER).

So far, only reference electrodes of the first kind that have been realized in liquid chromatographic cells are on the basis of solid electrodes. The reference potential of reported solid electrodes for low dead volume liquid chromatographic cells is dependent on changes of electrolyte composition other than the changes in the concentration of hydronium ions. Such electrodes are called pseudo or quasi reference electrodes, and examples of quasi reference electrodes are disclosed by U.S. Pat. No. 4,404,065 to MATSON or U.S. Pat. No. 5,368,706 to BOWERS et al. Important examples of such solid quasi electrodes are palladium (Pd) or palladium oxide (PdOx) reference electrodes used in electrochemical detection cells for liquid chromatography. In the disclosed example of liquid chromatographic cells the counter electrodes are also made of Pd or PdOx. An important limitation of quasi reference electrodes is their instability of reference potential under the conditions of gradient elution in liquid chromatography. That limitation makes the use of detection cell containing the quasi reference electrodes impossible. The reference potential of PdH electrode, on the other hand, does not change at all or does not change to a degree preventing the use of PdH as reference electrodes under the conditions of liquid chromatographic detection. The only significant change of reference potential of PdH occurs under the conditions of a pH gradient. Such change is predictable and defined by Nernst equation in the same way as for example for glass membrane pH indicator electrodes. For example, pH indicator electrodes can compensate for pH induced changes of response of working electrodes (see, e.g., WELCH et al., "Comparison of Pulsed Coulometric Detection and Potential-Sweep Pulsed Coulometric Detection for Underivatized Amino Acids in Liquid Chromatography," Anal. Chem., 1989, vol. 61, pp. 555-559). The compensative action of pH sensing reference electrodes such as glass membranes but also PdH electrodes achieves baselines which are unaffected by pH gradients in the form of so called gradient rise or of other similar artifacts. A working electrode with an applied potential referenced to a pH indicator electrode produces a response only in the presence of an electroactive analyte and not as a result of change in pH.

Another example of solid state quasi reference electrode made with Pd or a palladium compound is the $Pd/PdI_2$ electrode disclosed by U.S. Pat. No. 6,572,748 to HERRMANN et al. This reference electrode is formed by depositing a metallic palladium layer by thick film technology. Then, the palladium layer is covered by a suitable palladium compound layer through an electrolytic process or through a precipitation.

Palladium-hydrogen (PdH) electrodes in combination with a suitable reference electrode may be used as pH sensors and/or as proton generation electrodes for aqueous and non-aqueous coulometric titrations. See, e.g., SCHWING et al. "COMPARISON OF DIFFERENT PALLADIUM-HYDROGEN ELECTRODE AS pH INDICATORS," Analytica Chimica Acta, 1956, vol. 15, pp. 379-388; STOCK et al. "THE PALLADIUM ELECTRODE IN AQUEOUS AND NON-AQUEOUS TITRIMETRY", Analytica Chimica Acta, 1959, vol. 20, pp. 73-78; and DOBSON, "The PallapHode Electrode System," Platinum Metals Rev., 1981), vol. 25, no. 2, pp. 72-73.

The palladium-hydrogen electrodes for such purposes are prepared by depositing palladium black upon a platinum, gold, or palladium film. The palladium-hydrogen electrode is then created by adsorption of hydrogen from water electrolysis. During the electrolytic process, the source potential for water electrolysis is not controlled. On the other hand, the electrolytic current and time are monitored and controlled. The electrolytic current is high, as much as 50 mA (see SCHWING). This is at least four orders of magnitude higher than the current values suitable for chromatographic detection cells. The currents of the magnitude common in coulometric titrations would generate excessive noise of the detection signal if applied to a reference electrode of an electrochemical detection cell utilized for chromatographic applications.

Other optimized palladium-hydrogen electrodes for use as pH reference electrode were utilized in potentiometric and voltammetric experiments performed in bulk solutions. See, e.g., GOFFE et al., "Internally charged palladium hydride reference electrode-Part 1: The effect of charging current density on long-term stability," Medical & Biological Engineering & Computing, 1978, vol. 16, pp. 670-676 (hereinafter "GOFFE"; and KELLY et al., "Internally charged palladium hydride reference electrode: II Automatically controlled palladium hydride electrode," Medical & Biological Engineering & Computing, 1981, vol. 19, pp. 333-339 (hereinafter "KELLY"). Such palladium-hydride reference electrodes were prepared and maintained by continuous internal charging with a power source. The charging current was monitored and controlled for achieving long-term stability of reference potential. On the other hand, the charging potential was not controlled at all even though it was shown that the applied potential dramatically affected the reference potential of the palladium-hydrogen electrode.

So far, solid state reference electrodes of the palladium-hydrogen type have been described only for use in a bulk solution. See, e.g., FLEISCHMANN et al., "A palladium-hydrogen probe electrode for use as a microreference electrode," J. Scientific Instruments, 1968, series 2, vol. 1, pp. 667-668 (hereinafter "FLEISCHMANN"); MUNASIRI et al., "Palladium-hydrogen electrodes for coulometric titration analysis of acids and bases," J. Electroanal. Chem., 1992, vol. 332, pp. 333-337 (hereinafter "MUNASIRI"); "$Pd/H_2$ REFERENCE ELECTRODE", date unknown, Cormet Testing Systems, Helsinki, Finland (hereinafter "Cormet"). See http://www.cormet.fi/pdf/PDF_Pd—H2.pdf. To date, it does not appear that there has been a single report describing the use of such electrodes in flow through chromatographic detection cells.

In the majority of cases, palladium-hydrogen electrodes are prepared and maintained without using a secondary power source providing a continuous supply of hydrogen to the palladium electrode. For, example, palladium-hydrogen electrodes are prepared by treating palladium with hydrogen generated from a non-continuous electrolytic process (see, e.g., FLEISCHMANN and MUNASIRI) or from a pressurized gas cylinder (see, e.g., Cormet). In one commercial example, $Pd/H_2$ electrode is maintained at a saturated state with hydrogen gas from a cylinder for achieving a stable reference potential (see, e.g., Cormet). Such bubbling of hydrogen gas through the solution not only at the reference electrode but also in the vicinity of working and counter electrodes would cause excessive noise levels in the flow through cells, and is thus completely unacceptable for chromatographic detection cells.

In another example, palladium-hydrogen electrodes are prepared by cycling a Pd wire between negative and positive polarity and maintaining a constant current density (see FLEISCHMANN). During use, the $PdH_2$ electrode was disconnected from the power supply. The palladium-hydrogen electrode thus prepared offered a stable reference potential for up to 24 hours. Then, the palladium-hydrogen electrode needed to be charged with electrolytically generated hydrogen again by cycling it again in acidic solution.

During discontinuous charging, the palladium is converted to various forms of palladium hydride, i.e. $\alpha$, $\alpha+\beta$, $\beta$ phases. The phases are defined by the ratio of H/Pd (see, e.g., DOBSON et al., "Some Experimental Factors which Govern the Potential of the Palladium Hydride Electrode at 25 to 195°

C.," J. Chem. Soc., Faraday Trans. 1, 1972, vol. 68, pp. 749-763; DOBSON et al., "Plateau Potentials of the α+β Palladium Hydride Electrode at Temperatures between 25 and 195° C.," J. Chem. Soc., Faraday Trans. 1, 1972, vol. 68, pp. 764-772. Without a continuous supply of hydrogen from the outside, the palladium-hydride phases loose their hydrogen content and convert back to pure palladium. and thus recharging of the reference electrode becomes necessary.

Past attempts to avoid bubble formation at the sensing end of continuously charged PdH electrodes used as pH indicator electrodes led to a creation of the so called "internally charged" electrodes (see, e.g., SCHWING. and GOFFE and Kelly) which are exemplifying in the available literature the format of PdH electrodes with a continuous connection to power and without the need for recharging.

The electrode of this type include a palladium wire continuing from a sealed internal chamber into the bulk of a sample solution. A suitable counter electrode is also contained in the internal chamber. The internal portion of the palladium wire and the counter electrode are immersed in a suitable electrolyte contained in the internal chamber. The continuous supply of hydrogen to the Pd electrode is maintained by a constant current supplied to the pair of electrodes in the internal chamber. However, it must be noted, that this format of continuous recharging of PdH electrodes requires a bulky design of the complete electrode assembly with similar limitations to miniaturization as is the case with a reference electrode of the second kind (e.g., silver/silver chloride, calomel etc). Another drawback of internally charged PdH electrodes is the limitation of their lifetime by the amount of protons obtainable to the Pd electrode in the internal chamber at the range of potentials selected for the internal charging of such electrode. This aspect of internally charged PdH electrodes is similar to the lifetime limitations of electrodes of the second kind based on the limited supply of conductive salt in the liquid junctions of electrodes of the second kind.

To date, internally charged PdH electrodes designed by SCHWING and others have not been adapted for use with low internal volume (1 pL to 1 μL) chromatographic detection cells and neither have been continuously charged palladium-hydrogen electrodes without an internal chamber. The potential usefulness of such electrodes on one hand and the considerable delay of their implementation in chromatographic cells on the other hand indicate that both types of continuously charged PdH electrodes have been deemed unsuitable for use in the low volume flow-through chromatographic detection cell by those skilled in the art until present. It is interesting to observe that similar limitations as with PdH electrodes were encountered with platinum-hydrogen (PtH$_2$) electrodes. See, e.g., GINER, J., "A Practical Reference Electrode," Electrochem. Soc., 1964, vol. 111, p. 376. The fully functional design of PtH$_2$ with continuous resupply by electrolytic hydrogen was reported already in 1964. However, a format of the same electrode suitable for use in chromatographic flow through detection cells has not yet been reported.

There appear to be formidable obstacles that prevent solid reference electrodes of the first kind for chromatographic three electrode cells of the thin layer type (internal volume 1 pL to 1 μL). First, hydrogen generation at a Pt or Pd substrate requires a presence of a counter electrode, or a second electrode of the reference electrode system, adding to the overall complexity of the detection cell design. Second, bubble formation (e.g., hydrogen gas at cathode, oxygen gas at anode) required for the maintenance of hydrogen electrodes could be considered incompatible with the thin-layer design of known chromatographic detection cells. Third, the power supply circuitry of the reference electrode module has to be integrated into the electronics that is driving the remaining two electrodes and also processing the resulting signal.

Palladium (Pd) has been considered a poor substitute for platinum (Pt) in the metal based hydrogen electrodes because of the lower catalytic activity of Pd for the formation of hydrogen from protons (see, e.g., IVES et al., Reference Electrodes Theory and Practice, 1961, p. 111, Academic Press, New York). Some workers had reported PdH electrodes to be less reliable than Pt-based electrodes (see, e.g., SCHWING).

It would therefore be useful to provide a detection cell with a reference electrode assembly which overcomes the above and other disadvantages of known reference electrodes used in low dead volume (1 pL to 1 μL) electrochemical detection cells.

BRIEF SUMMARY OF THE INVENTION

One aspect of the present invention is directed to a detection cell for a chromatography system including a cell body having an inlet, an outlet, and a counter electrode, a working electrode, a sample flow passageway extending between the inlet and the outlet and in fluid contact with the counter and working electrodes, and a palladium/noble metal reference electrode system.

The detection cell may be a three-electrode detection system.

The cell body may be formed of a conductive material. The cell body may be formed of a corrosion resistant metal or a conductive polymer. The cell body may be formed of a material selected from the group consisting of titanium, corrosion resistant alloy, stainless steel, carbon-loaded polyetherether ketone (PEEK), polythiophene, polyindole, and polynaphtalene.

The reference electrode system may be a palladium/platinum (Pd/Pt) reference electrode system. The reference electrode system may include a reference electrode of the first kind. The reference electrode system may include a palladium (Pd) reference electrode and a platinum (Pt) auxiliary electrode, both reference and auxiliary electrodes being in electrical contact with the fluid sample passageway. The palladium (Pd) reference electrode may include a wire extending into a reference electrode bore of the cell body. The reference electrode may be connected, directly or indirectly, to a negative pole of a power supply. The auxiliary electrode may be connected, directly or indirectly, to a positive pole of a power supply.

The detection cell may further include a gasket disposed between the counter and working electrodes and having a cutout forming a thin-layer channel between the counter and working electrodes, wherein the channel may be fluidly connected to the inlet and the outlet of the cell body thereby forming a portion of the fluid sample passageway.

The a cell body may include an inlet and an electrode cavity fluidly connected to the inlet and the outlet thereby forming a portion of the fluid sample passageway. At least one of the Pd reference electrode and the Pt auxiliary electrode may be a wire.

Another aspect of the present invention is directed to a chromatography system including any of the above-described detection cells. The chromatography system may include a plurality of detection cells, wherein the detection cells may be arranged in series.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIG. 3 is a schematic view of an exemplary three-electrode, ultra low volume chromatographic detection cell in which both electrodes constituting the PdH electrode are placed in the same polymeric block as the working electrode.

DETAILED DESCRIPTION OF THE INVENTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention (s) is/are intended to cover not only the exemplary embodiments, but also various alternatives, modifications, equivalents and other embodiments, which may be included within the spirit and scope of the invention as defined by the appended claims.

Figure 1:
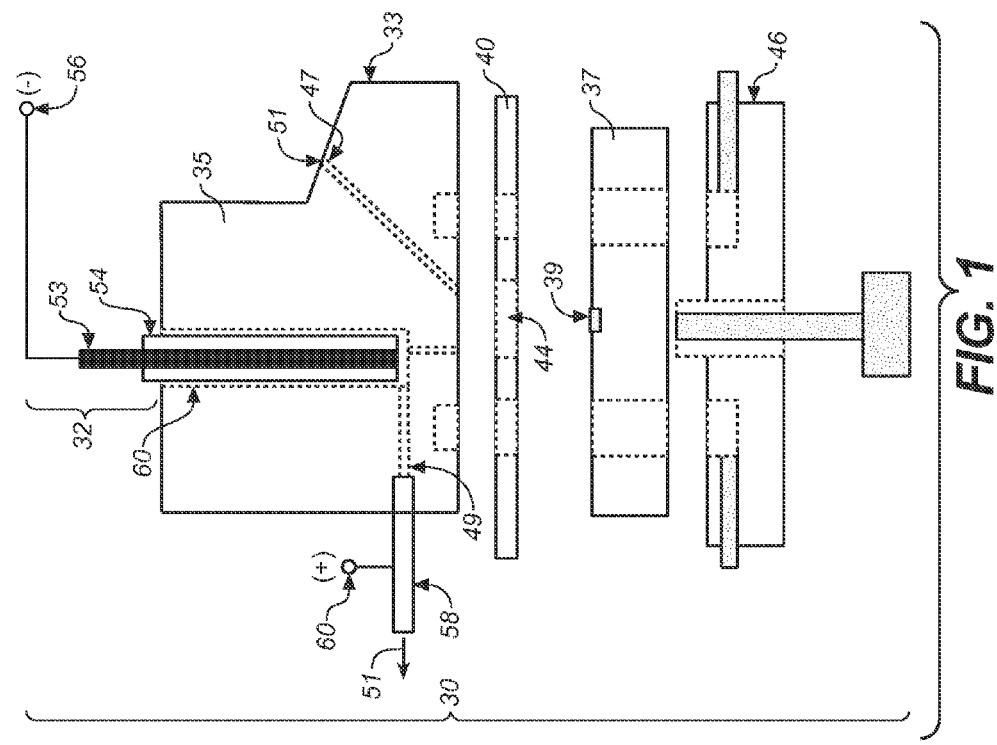
FIG. 1 is a schematic view of an exemplary detection cell for a chromatography system in accordance with various aspects of the present invention.

Turning now to the drawings, wherein like components are designated by like reference numerals throughout the various figures, attention is directed to FIG. 1, which illustrates an exemplary chromatographic detection cell generally designated 30. Various aspects of the detection cell are similar to the detectors found in the ICS-3000 Liquid chromatography System provided by Dionex Corporation of Sunnyvale, Calif., and in particular, similar to Dionex Corporation's ED40, ED50, and ED50A detectors. One will appreciate, however, that the detection cell of the present invention may be utilized on other chromatography systems.

In various embodiments of the present invention, the detection cell includes a reference electrode assembly 32 of a three-electrode cell 33, as is depicted in FIG. 1. One will appreciate, however, that a detection cell may have two or more electrodes in accordance with various embodiments, configurations, and design considerations. The older two electrode design uses the same two electrodes (working and reference) for adjustment of voltage and for current measurement whereas in three-electrode cells only the voltage is adjusted between the reference and working electrodes. The current measurements are taken between the working electrode and the counter electrode. The counter electrodes are called auxiliary electrodes by some. However, in the context of this text the term auxiliary electrode is reserved for the second, anodic electrode of the two-electrode cell of constituting the PdH electrode. There are reports describing chromatographic detection cells with more than three electrodes, for example, containing multiple working electrodes referenced to the same reference electrode (LUNTE et al, "Difference Mode Detection with Thin-Layer Dual-Electrode Liquid Chromatography/Electrochemistry," Anal. Chem., 1985, vol. 57, pp. 1541-1546). The PdH electrode which is described here can be used with all of the above types of low dead volume chromatographic detection cells.

The resulting chromatographic detection cell 30 includes many components similar to those found in Dionex Corporation's PED, ED50, and ED detectors, including a conductive cell body 35 serving as a counter electrode, a working electrode block 37 including a working electrode 39, a gasket 40 disposed between the counter and working electrodes and having a cutout forming a thin-layer channel 44, and yoke-knob assembly 46 for assembling the detection cell.

Suitable materials for cell body 35 include, but are not limited to, titanium, high quality stainless steel or sturdy high conductive polymers. The cell body is preferably machined or otherwise formed to include an inlet 47 and an outlet 49 which are fluidly connected with thin-layer channel 44 to form a fluid sample line 51. Preferably the inlet, channel and outlet are configured so as to minimize dead volume within the detection cell. In the illustrated configuration the thin layer path of the cell is formed by the gasket's channel, however, one will appreciate that the thin-layer path of the cell can be formed by a microscopic groove machined in the body of the conductive counter electrode.

For the purposes of the present invention, thin-layer channels are those with a volume in the range from 1 pL to 1 µL. The following ranges of flow path dimensions either within a gasket or as a finely machined microscopic groove can be used to form the low volume, thin layer flow path. Overall dimensions of the flow path may include a width of approximately 0.1-3 mm, a length of approximately 6-12 mm, and a thickness of approximately 0.0125-0.5 mm. Preferable they include a width of approximately 0.5-2 mm, length of approximately 6-10 mm, and a thickness of approximately 0.0125-0.25. Most preferably, they include a width of approximately 0.5-1.5 mm, a length of approximately 6-9 mm, and a thickness of approximately 0.0125 to 0.05 mm.

Yoke-knob assembly 46 allows for quick assembly and disassembly of detection cell 30 in an otherwise known manner. In particular, the yoke-knob assembly includes a yoke for aligning working electrode 39 against gasket 40, and in turn, against cell body 35 to sealingly engage the working electrode, gasket and cell body against one another. One will appreciate that the yoke-knob assembly may be configured to provide a consistent sealing force, for example, an approximately 5 lb/in$^2$ pressure against the working electrode in order to suitably and reliably maintain the sealing action of the gasket against both the working electrode and the cell body.

In contrast to prior detectors which include a relatively bulky silver/silver chloride reference electrode, detection cell 30 includes a palladium/platinum (Pd/Pt) reference electrode system 32 (Pd part). In the illustrated embodiment, the reference electrode system (Pt part) includes a palladium (Pd) reference electrode 53 extending into a reference electrode bore 54 of cell body 35. The reference electrode is connected, directly or indirectly, to a negative pole 56 of a suitable power supply. Preferably, the reference electrode is a wire. The compact nature of the wire reference electrode allows sufficient electrical contact with fluid sample line 51 while minimizing dead volume. One will appreciate that the reference electrode may have other configurations such as the ones illustrated in FIG. 2 and FIG. 3. The Pd electrode and its auxiliary electrode can come in the shape of foil, tube, net, grid, screen printed layer on a polymeric substrate or a thin layer on a polymeric substrate deposited by one of the sputtering coating techniques such as physical vapor deposition, chemical vapor deposition etc. The suitable materials for the substrate electrode for hydrogen include not only palladium but also its alloys of various transition metals such as Pd—Ir, Pd—Pt, Pd—Ag, and etc.

In addition, the reference electrode system includes an auxiliary electrode 58 to complete the reference electrode system. The auxiliary electrode is positively charged being connected, directly or indirectly, to a positive pole 60 of a suitable power supply. One will appreciate that the auxiliary electrode may be tubular, in which case outlet 49 of fluid sample 51 line may run through the auxiliary electrode, or may be cylindrical in which case the outlet may run along the auxiliary electrode. One will also appreciate that other configurations may be utilized provided that the auxiliary is in conductive contact with fluid traveling through the fluid sample line. The suitable materials for the auxiliary electrode include platinum, palladium, glassy carbon and graphite. Other materials such gold, copper an aluminum were found unsuitable due to their anodic dissolution and plating out on the hydrogen substrate electrode (see, e.g., OTTERSON et al., "Absorption of Hydrogen by Palladium up to Hydrogen-Palladium Atom Ratios of 0.97," 1969, p. 1-15, NASA, Washington, D.C.). To the extent to which the contact area of the hydrogen substrate metal is blocked by a layer of an unsuitable metal, the reference electrode potential of the PdH electrode becomes unsuitable.

In operation and use, detection cell 30 is used in a manner similar to that of known detectors having a conventional silver/silver chloride reference electrode. For example, the Pd reference electrode 53 and the Pt auxiliary electrode 58 are connected to a power supply with the polarities indicated in FIG. 1. Additionally, the Pd reference electrode 53 is connected as a reference electrode to the electronic circuitry of the three-electrode detection system in an otherwise conventional manner. In a preferable configuration, the auxiliary electrode is positioned downstream from the working electrode and the counter electrode.

A hydrogen reference electrode is generated by applying a potential from the power supply connected to the Pd and Pt electrodes. Preferably, the potential is less than approximately 3 V, more preferably approximately 1.25-2 V, and most preferably approximately 1.5-1.7 V. Also, the potential is substantially constant, that is, it is subject to oscillations and/or other variations in voltage less than approximately 10 mV more preferably less than approximately 0.1 mV, and most preferably less than approximately 0.001 mV. The Pd reference electrode provides a hydrogen electrode that gives a steady reference potential with respect to a Ag/AgCl reference electrode immersed in the same solution. The actual difference of reference values can be measured with any one of various suitable methods. For example, for any new detection experiments, a correctly adjusted value of DC amperometric and pulsed electrochemical potentials can be recognized by achieving an approximately same level of baseline signal and similar peak areas as with the silver/silver chloride reference electrode. Alternatively, the reference potential of the Pd-reference-electrode-based hydrogen electrode can be evaluated by potential measurement compared against a conventional silver/silver chloride electrode installed in a second detection cell located downstream from the first detection cell.

In the majority of cases, the reference potential of the PdH is 50 mV vs. standard hydrogen electrode (SHE). In the same way as the potential of SHE, the potential of PdH changes with pH in Nernstian fashion by 59 mV per pH unit. The correct reference potential can then be calculated for any known pH as:

$$\text{Reference potential of PdH}=50-59\times\text{pH}$$

The Ag—AgCl referenced potentials then have to be adjusted for use with PdH electrodes thus:

$$\text{Potential for use with PdH electrode}=\text{Ag—AgCl referenced potential}-(\text{Reference potential of PdH}+205)$$

The value of 205 represents the value of Ag—AgCl potential vs. SHE.

Proper functioning of a Pd and Pt electrode pair connected to a DC power source was evaluated in a transparent glass beaker and confirmed in a low dead volume flow through chromatographic detection cell. In the former experiment, the Pd was connected as a cathode and Pt as an anode. Both electrodes were immersed in an unstirred solution of 0.01 M NaOH which was kept at a room temperature. After both wires remained connected to 1.6 V for about 5 minutes, it was possible to observe using an approximately 5× magnifying glass an accumulation of miniature bubbles on the Pt electrode but not on the Pd electrode. In fact bubble accumulation was never observed on the Pd electrode. It remained free of bubbles during the entire duration of our experiment. This observation revealed that at a suitable value of voltage applied to the electrodes, all hydrogen created by the reduction of protons at the cathode was taken up into the Pd wire and creation of bubbles at the Pd reference electrode could be avoided and noise associated with the reference electrode is significantly reduced since a reference electrode in accordance with the present invention does not contribute to bubbling.

During the same experiment we have also observed that an accumulation of bubbles at the Pt electrode could be avoided by stirring the contents of the glass beaker. This experiment allowed us to conclude that in contrary to the conclusion of many published reports a construction of internal charging chamber for the PdH electrode could be avoided and that a continuously recharged PdH electrode could be built and function properly without an internal charging chamber. These conclusions were used in designing a configuration of the reference electrode system so that the Pt electrode was always located downstream of the Pd electrode and both electrodes were always exposed to a stream of liquid when used as a PdH reference electrode system. It is a well known fact that gas bubbles passing trough an electrochemical detection cell or trapped in an electrochemical cell are the cause of baseline deforming artifacts also known as spikes. The spikes coinciding with peaks of interest make quantitative analysis based on peak areas problematic. Working with the cell and reference electrode of FIG. 2, we were able to confirm the absence of baseline artifacts in multiple long-term experiments. The quality of baseline measured as noise was equivalent to that observed with well functioning reference electrodes of the second kind.

Advantageously, the present invention provides for a Pd-based hydrogen reference electrode which can be easily miniaturized for use in dead volume chromatographic detection cells. The present invention also allows for a Pd-based hydrogen reference electrode suitable for use in capillary system with extreme requirements for minimizing dead volume. An example of extremely low dead volume cell is illustrated in FIG. 3. The reference electrode system of the present invention produces a stable reference potential which does not change upon exposure to alkaline solvents. In addition, the reference electrode assembly of the present invention does not exude any ions interfering with proper functioning of other detectors connected downstream.

The configuration of the reference electrode assembly of the present invention allows for steady reference potential during long term exposure to alkaline column eluates. Advantageously, there is no accidental application of excessive detection potentials to the working electrode resulting in downward trending of detection response over time or in narrower range of linearity of calibration plots.

As the PdH reference electrode does not include any liquid junction as a typical reference electrode of the second kind, there is an absence of electrolytes exiting from the reference electrode (e.g. chloride ions exiting from the silver/silver chloride electrode). Generally, the reference electrode assembly of the present invention provides for a longer useful life as compared with conventional silver/silver chloride reference electrodes and other reference electrodes of a second kind.

Figure 2:
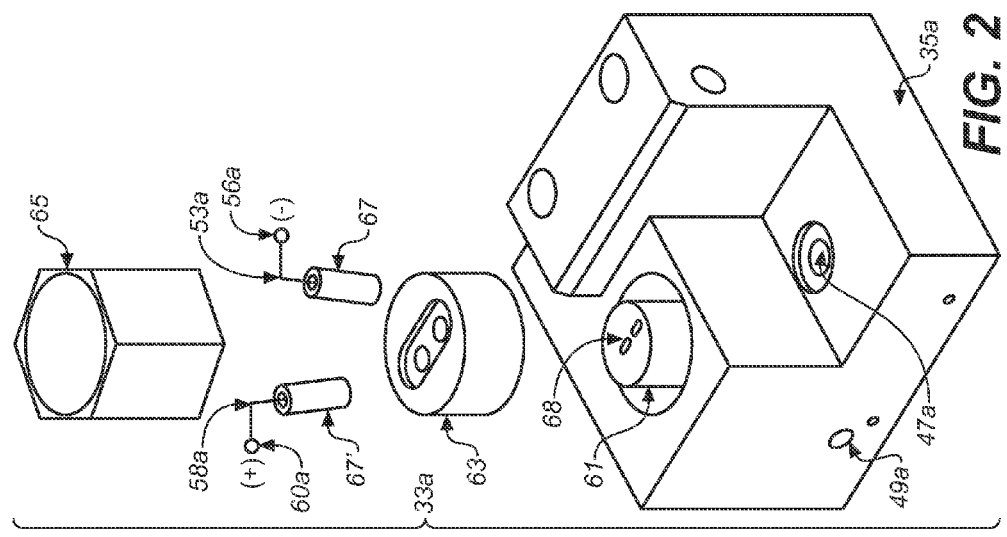
FIG. 2 is a perspective view of an exemplary upper portion of another exemplary detection cell for a chromatography system in accordance with various aspects of the present invention of the present invention.

In another exemplary embodiment of the present invention, detection cell 30a is similar to detection cell 30 described above but includes a reference electrode system 32a in which both the reference electrode and the auxiliary electrode are in the form of wires, as shown in FIG. 2. Like reference numerals have been used to describe like components of detection cell 30a is similar to detection cell 30.

In this embodiment, a Pd-based hydrogen electrode can be realized as a reference electrode assembly 32a containing a Pd reference electrode 53a and a Pt auxiliary electrode 58a, each in the form of a wire in close proximity with the other. Such a reference electrode system can be made to fit into existing reference electrode compartments that are designed for conventional silver/silver chloride reference electrodes.

For example, reference electrode system 32a may be configured to replace the large reference electrode cylinders of existing detection cells, for example, that of the ED50A or ED provided by Dionex Corporation of Sunnyvale, Calif. and illustrated in ED50A ELECTROCHEMICAL DETECTOR OPERATOR'S MANUAL, rev. 02, Nov. 2002 or in ICS-3000 Ion Chromatography System Operator's Manual (both manuals are available at http://www.dionex.com/en-us/webdocs/57752-31772_02_ED50A_V17.pdf and www.dionex.com/en-us/webdocs/48428-Man-IC-ICS-3000-System-Operators-2008-01-065031-04.pdf), the entire contents of the ED50 manual and the ICS3000 system manual is incorporated herein by this reference.

In this embodiment, detection cell 30a like the ED50A or ED detection cell, includes a cell body 35a having a threaded reference electrode cavity 61, a working electrode block, and a gasket disposed between the cell body and the working electrode block. An inlet 47a is fluidly connected to the bottom of the threaded reference electrode cavity. In this embodiment, the detection cell is provided with a reference electrode housing 63 that is secured within the threaded reference electrode cavity to position the ends of the electrodes in electrical contact with the fluid sample line.

Reference electrode housing 63 is secured within cavity 61 by a clamping nut 65, which nut allows one to releasably secure the reference electrode housing within cell body 35a. One will appreciate that the electrode housing may be releasably or permanently secured within the cavity by other suitable means including, but not limited to securing gaskets, press fittings, bayonet fittings or caps, welding, and etc.

Appropriate mountings 67, 67' secure the Pd reference electrode 53a and the Pt auxiliary electrode 58a within the housing. For example, 6-32 fittings and 1/16" tubing may be utilized to sealingly secure the wire electrodes within the housing. One will appreciate that suitable means may be utilized to secure the electrodes within the reference electrode housing such as a wire sleeve. One will also appreciate that the electrodes may be formed of wire or other suitable conductors such as rod, tube, foil, net or grid shaped conductors.

In this embodiment, a reference electrode gasket 68 may be provided which defines a thin-layer channel extending between Pd reference electrode 53a and the Pt auxiliary electrode 58a. Similar to gasket 40 described above, a thin-layer path of the cell by the reference electrode can be formed by a channel within reference electrode gasket 68 or may be formed by a microscopic groove machined in electrode housing 63 and/or cell body 35a of the conductive counter electrode. In either case, the channel and outlet is configured so as to minimize dead volume within the detection cell.

Figure 4:
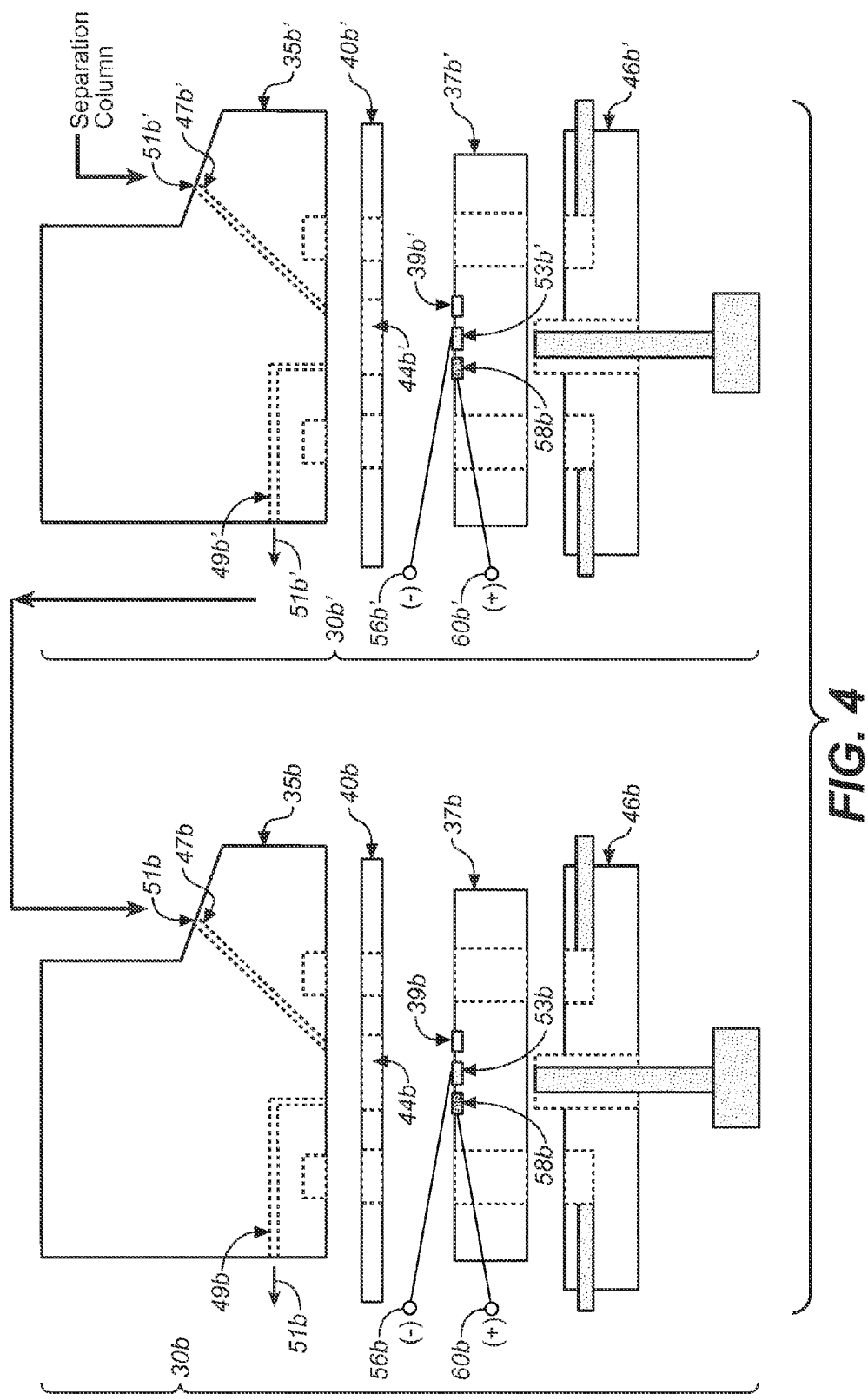
FIG. 4 is a schematic view of an exemplary chromatography system including a plurality of chromatographic detection cells in series.

In another exemplary embodiment of the present invention, detection cell 30b is similar to detection cells 30 and 30a described above in the form of a three-electrode, ultra low volume chromatographic detection cell. As shown in FIG. 3, various embodiments of the present invention may both electrodes constituting the PdH electrode be placed in the same polymeric block as the working electrode. And as shown in FIG. 4, various embodiments are directed to a chromatography system including a plurality of detection cells 30b, 30b' arranged in series with one another and operably connected to other components thereof such as a separation column, an electrolytic suppressor, and/or other components thereof. One will appreciate that two, three or more detection cells may be arranged in series with one another.

In operation and use, detection cells 30a, 30b, 30b' are used in substantially the same manner as detection cell 30 discussed above.

In many respects various modified features of the various figures resemble those of preceding features and the same reference numerals followed by subscripts "a" designate corresponding parts.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A detection cell for a chromatography system, the detection cell comprising:
    a cell body including a counter electrode;
    a working electrode block including a working electrode;
    a gasket separating the working electrode block from the cell body, the gasket defining a sample flow passageway extending between an inlet and an outlet of the detection cell and in fluid contact with the cell body and the working electrode; and
    a reference electrode system in fluidic contact with the outlet and including an auxiliary electrode operably connected to a positive pole of a power supply and a palladium/hydrogen (PdH) reference electrode operably connected to a negative pole of the power supply.

2. A detection cell according to claim 1, wherein the detection cell is a three-electrode detection system.

3. A detection cell according to claim 1, wherein the cell body is formed of a conductive material.

4. A detection cell according to claim 1, wherein the cell body is formed of a corrosion resistant metal or a conductive polymer.

5. A detection cell according to claim 4, wherein the cell body is formed of a material selected from the group consisting of titanium, corrosion resistant alloy, stainless steel, carbon-loaded polyetherether ketone (PEEK), polythiophene, polyindole, and polynaphtalene.

6. A detection cell according to claim 1, wherein the reference electrode system includes a reference electrode of the first kind.

7. A detection cell according to claim 1, wherein the palladium/hydrogen (PdH) reference electrode and the auxiliary electrode are in electrical contact with the fluid sample passageway, and wherein the auxiliary electrode includes a platinum electrode.

8. A detection cell according to claim 7, wherein the palladium/hydrogen (PdH) reference electrode includes a wire extending into a reference electrode bore of the cell body.

9. A detection cell according to claim 1, wherein the a cell body includes an electrode cavity fluidly connected to the inlet and the outlet thereby forming a portion of the fluid sample passageway.

10. A detection cell according to claim 9, wherein at least one of the PdH reference electrode and the auxiliary electrode is a wire.

11. A chromatography system comprising the detection cell according to claim 9.

12. A chromatography system comprising the detection cell according to claim 1.

13. A chromatography system comprising a plurality of detection cells according to claim 1, wherein the detection cells are arranged in series.

14. A detection cell for a chromatography system, the detection cell comprising:
a cell body;
a working electrode block including a working electrode;
a sample channel extending between an inlet and an outlet of the detection cell and in fluid contact with the cell body and the working electrode;
a counter electrode in fluid contact with the sample channel; and
a reference electrode system in fluidic contact with the outlet and including an auxiliary electrode operably connected to a positive pole of a power supply and a palladium/hydrogen (PdH) reference electrode operably connected to a negative pole of the power supply.

15. A detection cell according to claim 14, wherein the cell body is formed of a conductive material.

16. A detection cell according to claim 14, wherein the palladium/hydrogen (PdH) reference electrode and the auxiliary electrode are in electrical contact with the sample channel, and in which the auxiliary electrode includes a platinum electrode.

17. A detection cell according to claim 14, wherein the palladium/hydrogen (PdH) reference electrode includes a wire extending into a reference electrode bore of the cell body.

18. A detection cell according to claim 14, wherein the reference electrode system operates at a potential less than approximately 3V subject to variations in voltage of less than approximately 10 mV.

19. A detection cell according to claim 14, wherein the channel has a volume of approximately 1 pL to 1 μL.

* * * * *